(12) United States Patent
Cai

(10) Patent No.: US 7,571,061 B2
(45) Date of Patent: Aug. 4, 2009

(54) NON-DESTRUCTIVE METHOD OF MEASURING A MOISTURE CONTENT PROFILE ACROSS A HYGROEXPANSIVE, COMPOSITE MATERIAL

(75) Inventor: Zhiyong Cai, Madison, WI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/079,868

(22) Filed: Mar. 28, 2008

(65) Prior Publication Data

US 2008/0262752 A1 Oct. 23, 2008

Related U.S. Application Data

(60) Provisional application No. 60/923,946, filed on Apr. 17, 2007.

(51) Int. Cl.
*G06F 19/00* (2006.01)
*G01B 15/00* (2006.01)

(52) U.S. Cl. ......................................... 702/40; 702/155
(58) Field of Classification Search .................. 702/38, 702/40, 155, 156; 264/406, 410; 250/339.12; 324/637
See application file for complete search history.

(56) References Cited

U.S. PATENT DOCUMENTS

| 3,693,079 A | 9/1972 | Walker |
| 4,831,545 A * | 5/1989 | Floyd et al. .................... 702/40 |
| 4,884,288 A | 11/1989 | Sowerby |
| 4,885,759 A | 12/1989 | Tomoda et al. |
| 4,941,357 A | 7/1990 | Schajer |
| 5,023,805 A * | 6/1991 | Aune et al. .................... 702/38 |
| 5,488,312 A | 1/1996 | Havener et al. |
| 5,621,391 A | 4/1997 | Elseth |
| 5,960,104 A | 9/1999 | Conners et al. |
| 6,359,446 B1 * | 3/2002 | Little, Jr. .................... 324/637 |
| 6,526,119 B1 | 2/2003 | Lappalainen et al. |
| 6,708,555 B1 | 3/2004 | Lyons, Jr. et al. |
| 6,757,354 B2 | 6/2004 | Skatter et al. |
| 7,043,970 B2 | 5/2006 | Ristea et al. |

(Continued)

FOREIGN PATENT DOCUMENTS

WO    WO 91/05245    4/1991

(Continued)

OTHER PUBLICATIONS

Dennis, J.R. and F.C. Beall. 1977. Evaluation of a new portable radiofrequency moisture meter on lumber with drying gradients. Forest Prod. J. 27(8).

(Continued)

*Primary Examiner*—Bryan Bui
(74) *Attorney, Agent, or Firm*—John D. Fado; Lesley D. Shaw; Janet I. Stockhausen

(57) ABSTRACT

The teachings provided herein are generally directed to a non-destructive method of measuring a moisture content profile across a dimension of a hygroexpansive, composite material using radiation and a volumetric shrinkage correction. The measurement of a series of moisture content profiles over time can provide, for example, a measure of the movement of moisture during the process of drying of the composite material.

31 Claims, 7 Drawing Sheets

U.S. PATENT DOCUMENTS

| | | | |
|---|---|---|---|
| 7,068,050 | B2 | 6/2006 | Steele et al. |
| 7,129,713 | B2 | 10/2006 | Katz |
| 7,149,633 | B2 | 12/2006 | Woods et al. |
| 2005/0101024 | A1* | 5/2005 | Mbachu et al. ............... 436/85 |
| 2006/0201022 | A1 | 9/2006 | Logan |

FOREIGN PATENT DOCUMENTS

| | | |
|---|---|---|
| WO | WO 2007/028856 | 3/2007 |

OTHER PUBLICATIONS

Feng, Y. and O. Suchsland. 1993. Improved technique for measuring moisture content gradient in wood. Forest Prod. J. vol. 43(2).

Hattori, Y. and Y. Kanagawa. 1985. Nondestructive measurement of moisture distribution in wood with a medical x-ray CT scanner I. Accuracy and influencing factor. J. of the Japan Wood Res. Society, 31(12).

James, W.L. 1963. Electric moisture meters for wood. USDA Forest Service Res. Note FPL-08. Forest Prod. Lab., Madison, Wis.

Kanagawa, Y. and Y. Hattori. 1985. Nondestructive measurement of moisture distribution in wood with a medical x-ray CT scanner II. Changes in moisture distribution with drying. J. of the Japan Wood Res. Society, 31(12).

Loos, W.E. 1961. Applications of the gamma-ray backscatter technique to the inspection of utility poles. For. Prod. J. 11(8) 333-36.

Loos, W.E. 1965. A review of methods for determining moisture content and density of wood by nuclear radiation techniques. For. Prd. J. 15(3).

Loos, W.E. 1965. The relationship between gamma-ray absorption and wood moisture content and density. For. Prd. J. 11(3).

Myer, J.T. and L.W. Rees. 1926. Electrical resistance of wood with special reference to the fiber-saturation point. New York Coll. of Forestry at Syracuse Univ. Tech. Bull. No. 19.

Xu, W., P.M. Winistorfer, and W.W. Moschler. 1996. A procedure to determine water absorption distribution in wood composite panels. Wood and Fiber Science, 28(3).

U.S. Department of Energy, Energy Efficiency and Renewable Energy. Wireless Microwave Wood Moisture Measurement System for Wood Drying Kilns. Jan. 2007 [online], [retrieved on Mar. 21, 2008] Retrieved from the Internet using Internet <Url: http://www1.eere.energy.gov/industry/forest/pdfs/wireless_microwave.pdf.

Wagner Electronics website, MC4000 Advanced In-Kiln Measurement System, Nov. 9, 2006, [online], [retrieved on Mar. 21, 2008] Retrieved from the Internet Archive Wayback Machine using Internet <URL: http://web.archive.org/web/20061109124153/http://www.wwwagner.com/mc4000.php http://www.wwwagner.com/mc4000.php.

Coe Newnes McGehee website, In-Kiln Moisture Measurement System, Oct. 23, 2006, [online], [retrieved on Mar. 21, 2008] Retrieved from the Internet Archive Wayback Machine using Internet <URL: http://web.archive.org/web/20061023075430/http://www.coemfg.com/products/drykiln/accudry.php http://www.coemfg.com/products/drykiln/accudry.php.

Delmhorst Instrument Company website, KIL-MO-TROL, Oct. 27, 2006, [online], [retrieved on Mar. 21, 2008] Retrieved from the Internet Archive Wayback Machine using Internet < URL: http://web.archive.org/web/20061027080323/http://www.delmhorst.com/products_kilmotrol.html http://www.delmhorst.com/products_kilmotrol.html.

Lignomat USA Ltd. Inc. website, Wireless Probes Revolutionize Moisture Measurement When Drying Wood, Oct. 24, 2006, [online], [retrieved on Mar. 21, 2008] Retrieved from the Internet Archive Wayback Machine using Internet <URL: http://web.archive.org/web/20061024162315/http://www.lignomat.com/wireless.htm http://www.lignomat.com/wireless.htm.

Aqua Measure Instrument Company website, Moisture Register Products, Dec. 6, 2006, [online], [retrieved on Mar. 21, 2008] Retrieved from the Internet Archive Wayback Machine using Internet <URL: http://web.archive.org/web/20061206193303/http://www.aquameasure.com/ http://www.aquameasure.com/.

DryTrack, LLC website, DryTrack System [online], [retrieved on Mar. 21, 2008] Not Retrievable from the Internet Archive Wayback Machine http://www.drytrack.com/product.html.

Eklund, B.A. 1957. The fiber saturation point of wood as determined with radiosotopes. Master of Sci. Thesis, Univ. Calif.

* cited by examiner (a)

(b)

NON-DESTRUCTIVE METHOD OF MEASURING A MOISTURE CONTENT PROFILE ACROSS A HYGROEXPANSIVE, COMPOSITE MATERIAL

STATEMENT REGARDING FEDERALLY SPONSORED RESEARCH OR DEVELOPMENT

The U.S. Government has certain rights in the inventions disclosed herein.

BACKGROUND OF THE INVENTION

1. Field of the Invention

The teachings generally relate to a non-destructive method of measuring a moisture content profile across a dimension of a hygroexpansive, composite material using radiation and a volumetric shrinkage correction.

2. Description of the Related Art

Moisture gradients in hygroscopic, composite materials, such as wood, are known to affect internal stresses that cause dimensional changes and eventual development of defects. Severe deformation and other defects of finished products reduce product quality and have the potential to damage a manufacturer's reputation and significantly increase the cost of manufacturing.

One of the oldest methods for measuring moisture gradient in wood was the bandsaw slicing technique. This technique is not entirely accurate due to the kerf and moisture losses caused by heat generated during high speed cutting. The methods of slicing thin layers were improved later by using a drill bit and a microtone knife. Since the samples were destroyed after measuring the moisture gradient, these methods failed to provide a continuous monitoring of moisture movements inside the samples. This made it difficult to develop accurate models of moisture gradient and movement during wood drying.

The search for a nondestructive method of measuring moisture in wood started in early 1900. The electrical resistance of wood was found to be a good indicator of its moisture content and was widely used after the extensive study on the electronic properties of wood. Instead of using single parameter (electrical resistance), many advanced devises employed radio frequency signals to measure moisture content in wood. These methods were based primarily on principles of electrical resistance, capacitance, and phase. Since the relationship between moisture content in wood and its electrical properties were not fully understood, the radiofrequency technique was dependent on the experimental data to create an empirical relationship for each species.

Warping of wood-based composites is a long-standing problem associated with secondary manufacturing processes, such as the drying of the wood products, in the wood panel industries. Severe warping of finished products has the potential to significantly increase the cost of manufacturing and lower the consumer's confidence in using wood composites. The Composite Panel Association (previously called the National Particleboard Association) considers warp to be the leading technical problem requiring further investigation.

Composite wood panels can be regarded as a multi-layered composite material, where each layer has a unique set of physical properties. Individual layers can be approximated as an orthotropic material having two principal directions. The mechanical behavior of layered composite materials is quite different from that of most common engineering materials which are homogeneous and isotropic. The makeup and physical properties of layered composites varies with location and orientation of the principal axes. Wood has unique and independent mechanical properties in the directions of three mutually perpendicular axes, so it may be described as an orthotropic material.

Linear expansion of wood composites usually includes thermal expansion and hygroscopic expansion. Both types of linear expansion perform about the same way, but hygroscopic expansion is more common and thermal expansion is relatively very small. Hygroscopic expansion is dependent on changes in moisture content, so moisture content change is the key parameter to determine the linear expansion once a panel is produced. Generally speaking, minimizing the moisture content change is the best way to keep panels from warping. For a panel with balanced construction, if the moisture content changes through its thickness are constant, there will be no induced out-of-plane stress. Therefore, there will be no warp. But for a panel with unbalanced construction, even if moisture content through the thickness changes uniformly, it is still possible to have out-of-plane deformation and warping problems. Balanced-construction composites are not necessarily free from warping. For a balanced panel, if there is an moisture content gradient through the thickness, the panel will still have a warping tendency.

Accordingly, one of skill will appreciate a non-destructive method of measuring moisture content, moisture content profiles, and the movement of moisture throughout a hygroexpansive, composite material such as wood. The wood product industry would benefit highly from a fast and accurate method of measuring moisture movement during drying processes, improving the design of drying processes, and preventing product damage associated with the removal of water during the drying of wood products.

SUMMARY

The teachings provided herein are generally directed to a non-destructive method of measuring a moisture content profile across a dimension of a hygroexpansive, composite material using radiation and a volumetric shrinkage correction, wherein the measurement of a series of moisture content profiles over time can provide, for example, a measure of the movement of moisture during a process of drying the composite material. In some embodiments, the method is a non-destructive method of measuring a moisture content in a hygroexpansive, composite material and comprises selecting a hygroexpansive material having an amount of water that results in a hygroexpansive state of the material and selecting a radiation source for emitting electromagnetic radiation such as, for example, x- or gamma radiation, into an entry surface of the composite material. In these embodiments, the radiation can have an intensity that is sufficient to penetrate through a depth of the composite material, a portion of the radiation is absorbed by the composite material, and a remainder of the radiation is transmitted from an exit surface of the composite material. In these embodiments, the distance between the entry surface and the exit surface is the depth of the composite material that was penetrated by the electromagnetic radiation. These embodiments further include measuring a density of the composite material in the hygroexpansive state, wherein the density is obtained by (i) passing the radiation through the composite material and (ii) measuring the amount of absorbed radiation.

In these embodiments, the amount of absorbed radiation provides the information to calculate the density of the composite material in the hygroexpansive state. These embodiments further include measuring a baseline density of a representative sample of the composite material in a water-free state, wherein the density is obtained by passing the radiation through the representative sample and measuring the amount of absorbed radiation. In these embodiments, the amount of absorbed radiation provides the information to calculate the density of the composite material in the water-free state. These embodiments further include determining a volumetric shrinkage of the representative sample that occurs during the removal of the amount of water from the representative material; and, calculating a moisture content of the composite material in the hygroexpansive state. The calculating includes using (1) the density of the composite material in the hygroexpansive state, (2) the density of the representative sample in the water-free state, and (3) the volumetric shrinkage of the representative sample in the water-free state.

In some embodiments, the teachings are directed to a nondestructive method of measuring a moisture content profile across a dimension of a hygroexpansive, composite material. In these embodiments, the method comprises selecting a hygroexpansive, composite material having an amount of water that needs to be removed prior to a predetermined end-use of the composite material and selecting a radiation source for emitting a thin collimated beam of an electromagnetic radiation into an entry surface of the composite material. In these embodiments, the radiation has an intensity that is sufficient to penetrate through a depth of the composite material, a portion of the radiation is absorbed by the composite material, and a remainder of the radiation is transmitted from an exit surface of the composite material. In these embodiments, the distance between the entry surface and the exit surface is the depth of the composite material that was penetrated by the radiation. These embodiments further include measuring a density profile of the composite material in a hygroexpansive state, wherein the density profile is obtained by (i) passing the radiation through the composite material and across a scanning direction of the composite material and (ii) measuring the amount of absorbed radiation at a plurality of locations across the scanning direction.

In these embodiments, a profile of the amount of absorbed radiation at each location across the scanning direction provides the information to calculate the density profile of the composite material in the hygroexpansive state. These embodiments further include measuring a baseline density profile of a representative sample of the composite material in a water-free state, wherein the density profile is obtained by (i) passing the radiation through the representative sample and across a scanning direction of the representative sample and (ii) measuring the amount of absorbed radiation at each location across the scanning direction. In these embodiments, a profile of the amount of absorbed radiation at each location simulates the baseline density profile of the composite material in the water-free state. These embodiments further include determining a volumetric shrinkage of the representative sample that occurs during the removal of the amount of water from the representative material to simulate a volumetric shrinkage of the composite material that occurs during removal of the amount of water; and, developing a moisture content profile of the composite material in the hygroexpansive state. In these embodiments, the developing includes calculating the moisture content at each point across the scanning direction of the composite material using (1) the density at each point across the scanning direction of the composite material in the hygroexpansive state, (2) the density at each point across the scanning direction of the representative sample in the water-free state, and (3) the volumetric shrinkage of the representative sample that occurs during the removal of the amount of water.

In some embodiments, the teachings are directed to a method of measuring moisture movement in a hygroexpansive, composite material during a water removal process. In these embodiments, the method comprises using the method of measuring a moisture content profile, as described above, to develop a first moisture content profile across the scanning direction at a first time, $t_1$; and repeating the method of measuring a moisture content profile at subsequent times $t_2$ through $t_n$ in a water removal process, wherein n is an integer greater than 2, times $t_2$ to $t_n$ each represent a period of time at which to measure subsequent moisture content profiles of each of a series of hygroexpansive states of the composite material that occur during the course of the water removal process, and $t_n$ represents the time at which the amount of water has been removed from the composite material. In these embodiments, the repeating provides a series of moisture content profiles that, when visualized together, provides a measure of the moisture movement in the hygroexpansive, composite material.

In some embodiments, the teachings are directed to a method of improving a process of removing water from a hygroexpansive, composite material. In these embodiments, the method comprises using the method of measuring moisture movement, as described above, and altering process variables in the water removal process to obtain desired moisture content profiles at times $t_1$ through $t_n$, wherein the variables are selected from a group consisting of variables in the design of a water removal apparatus, variables in the operation of the water removal apparatus, and variables in the design of the composite material.

In some embodiments, the hygroexpansive, composite material comprises a wood component. In some embodiments, the hygroexpansive, composite material is a particleboard or a waferboard. In some embodiments, the hygroexpansive, composite material is plywood. use of the equation $$m = \frac{\rho_m - \rho_0}{\rho_0} \times 100,$$

when m $\geq$ 30%, and use of the equation $$m = \frac{\rho_m - \rho_0}{\rho_0} \times 100 \times \frac{1}{\left(1 - \frac{10\rho_m S_0}{3\rho_0(1 - S_0)}\right)},$$

when m <30%.

In some embodiments, the electromagnetic radiation is x-radiation. In some embodiments, the electromagnetic radiation is gamma radiation. In some embodiments, the thin collimated beam has a width ranging from about 0.001 inches to about 0.020 inches and a length ranging from about 0.25 inches to about 4.0 inches at the entry surface of the hygroexpansive, composite material. In some embodiments, the radiation is x-radiation produced using a kilovoltage ranging from about 35 kV to about 300 kV. In some embodiments, the volumetric shrinkage ranges from about 2% to about 5%, from about 1% to about 25%, from about 1 to about 10%, from about 0.5% to about 3%, from about 1% to about 6%, or any range therein, from a hygroexpansive state to a water-free state.

In some embodiments, the baseline density across the scanning direction is substantially the same at each location, and the density at a single location is used as a constant baseline density in the calculation of moisture content.

In some embodiments, the measuring of the density profile of the composite material in the hygroexpansive state is continuous, in that the density profile is obtained by continuously (i) passing the radiation through the composite material and across the scanning direction of the composite material and continuously (ii) measuring the amount of absorbed radiation continuously across the scanning direction. In these embodiments, the profile of the amount of absorbed radiation as a continuous measurement across the scanning direction provides the information to calculate a continuous density profile of the composite material in the hygroexpansive state; and wherein, the repeating is done as described above and provides a series of continuous moisture content profiles that, when visualized together, provides a measure of the moisture movement in the hygroexpansive, composite material.

In some embodiments, the teaching is directed to an apparatus for detecting moisture content profiles of a hygroexpansive composite material. In these embodiments, the apparatus comprises a radiation source that is positioned for emitting an electromagnetic radiation in a first direction into an entry surface of a composite material in a hygroexpansive state. In these embodiments, the radiation has an intensity that is sufficient to penetrate through a depth of the composite material and transmit a remainder of the radiation from an exit surface of the composite material, wherein the distance between the entry surface and the exit surface is the depth of the composite material that was penetrated by the radiation.

In these embodiments, the apparatus also comprises a radiation detector that is positioned for processing the transmitted radiation from the first direction, wherein the processing includes (1) detecting the amount of electromagnetic radiation that penetrated the depth of the composite material and transmitted to the detector, and (2) converting the amount of radiation that transmitted to the detector into a digital signal corresponding to a density at a location in the composite material, and the density is used in computing the moisture content at the location in the composite material. In these embodiments, the apparatus also comprises a mechanism for moving the radiation source and the radiation detector in a scanning direction across a dimension of the composite material to acquire a series of the digital signals across the scanning direction. And, in these embodiments, the apparatus also comprises a computation system for translating each digital signal produced by the radiation detector in the scanning direction into the moisture content profile using (1) a density profile taken across the scanning direction of the composite material in the hygroexpansive state, (2) a density profile taken across the scanning direction of a representative sample of the composite material in a water-free state, and (3) a measure of volumetric shrinkage of the representative sample that occurs during the removal of the amount of water from the representative material.

In some embodiments, the teachings are directed to an apparatus for detecting moisture movement in a hygroexpansive composite material, wherein the apparatus comprises the apparatus for detecting moisture content profiles. In these embodiments, the computation system further comprises a translation engine embodied in a computer readable medium that calculates moisture movement by calculating moisture content profiles at each of times $t_1$ through $t_n$; wherein, n is an integer, $t_1$ through $t_n$ each represent a period of time at which to moisture content profiles of each of a series of hygroexpansive states of the composite material that occur at times $t_1$ through $t_n$ during the water removal process, and $t_n$ represents the time at which the amount of water has been removed from the composite material. In these embodiments, the computer system further comprises an automation module embodied in a computer readable medium for converting input parameters into an automated motion of the radiation source and the radiation detector, wherein the input parameters include scanning time, scanning speed, and scanning position. And, in some embodiments, the computer system further comprises a display.

DETAILED DESCRIPTION

The teachings provided herein are generally directed to a non-destructive method of measuring a moisture content profile across a dimension of a hygroexpansive, composite material using radiation and a volumetric shrinkage correction. The measurement of a series of moisture content profiles over time can provide, for example, a measure of the movement of moisture during a process of drying the composite material.

In some embodiments, the method is a non-destructive method of measuring a moisture content in a hygroexpansive material. The method comprises selecting a hygroexpansive, composite material having an amount of water that results in a hygroexpansive state of the material and selecting a radiation source for emitting electromagnetic radiation into an entry surface of the composite material. The density of the material in a hygroexpansive state can be used as an indirect measure of moisture content and can be measured by passing the radiation through the material and measuring the amount of radiation absorbed by the material. A baseline density of the material can then be determined using a representative sample of the material in a water-free state using the same procedure. A dimensional compensation is then used to correlate moisture content with density by taking the volumetric shrinkage of the representative sample that occurs during the removal of water. The moisture content is then calculated using the density of the material in the hygroexpansive state, the density of the representative sample in the water-free state, and the volumetric shrinkage of the representative sample in the water-free state.

Figure 1:
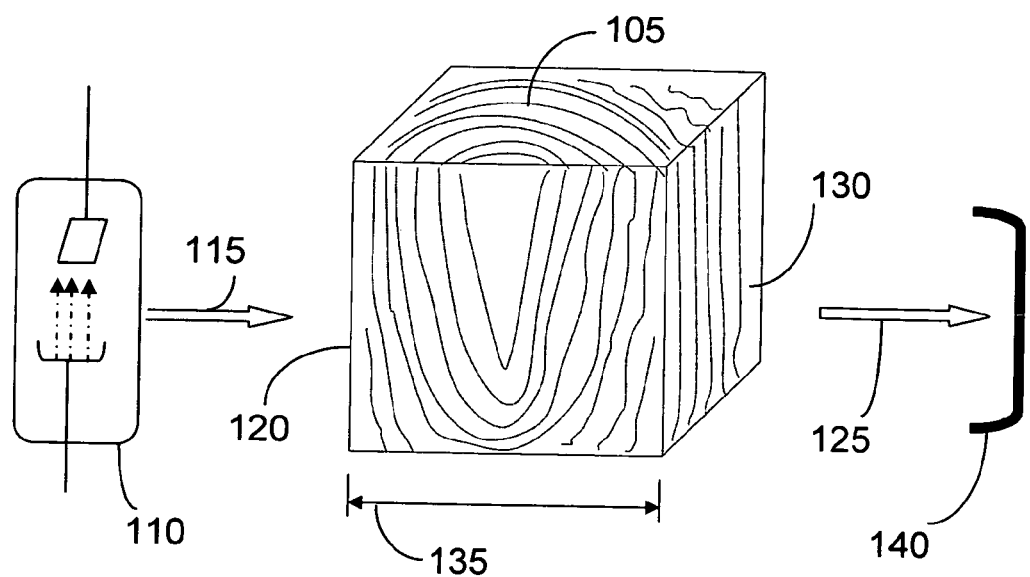
FIG. 1 illustrates the use of the method to measure a moisture content across a dimension of a wood material according to some embodiments.

FIG. 1 illustrates the use of the method to measure a moisture content across a dimension of a wood material according to some embodiments. The wood material 105 is selected, and a radiation source 110 is selected for emitting electromagnetic radiation 115 into an entry surface 120 of the wood material 105 in a hygroexpansive state. A portion of the radiation 115 is absorbed by the wood material 105, and a remainder 125 of the radiation 115 is transmitted from an exit surface 130 of the wood material 105. The distance 135 is the depth of the wood material 105 that was penetrated by the radiation 115. A representative sample of the wood material 105 is used to again measure the amount of radiation 115 that is transmitted from the representative sample in a water-free state and collected by a radiation detector 140. The amount of radiation 115 that is transmitted from the wood material 105 in the hygroexpansive state represents the density of the wood material 105 in the hygroexpansive state, and the amount of radiation 115 that is transmitted from the wood material 105 in the water-free state represents the density of the wood material 105 in the water-free state. The volumetric shrinkage is used as a dimensional compensation to correlate the density with a moisture content value.

The term "moisture content" generally refers to the amount of water in a material, for example a hygroexpansive, composite material, and the amount can be expressed in any units known to one of skill in the art. In some embodiments, the units can be expressed in percent by weight, for example, and can refer to the percent water based on the weight of the sample in its water free state. In some embodiments, the moisture content of a material can be greater than about 30% by weight and, in some embodiments, the moisture content of a material can be less than about 30% by weight. In some embodiments, the moisture content can range from In some embodiments, the moisture content can range from about 0.05% to over 200%, from about 0.5% to about 28%, from about 0.8% to about 25%, from about 1.2% to about 22%, from about 2.0% to about 20%, from about 3% to about 30%, from about 4% to about 15%, from about 5% to about 10%, from about 18% to about 25%, or any range therein. In some embodiments, the moisture content can range from about 30% to about 70%, from about 33% to about 50%, from about 35% to about 45%, from about 37% to about 42%, from about 31% to about 66%, or any range therein.

Without intending to be limited by any theory or mechanism of action, one of skill will appreciate that the water content of a hygroexpansive, composite material can change the physical properties of the material. Wood, for example, has an average fiber saturation point of about 30%, which is often considered as that moisture content below which the properties of wood begin to change as a function of moisture content. The dimension of the wood can remain the same when the moisture is above about 30%, but when the moisture content is drops below about 30%, the wood may start to shrink as a function of moisture content.

The term "hygroexpansive material" can refer to a material that experiences a change in volume with a change in moisture content. The term "hygroexpansive, composite material" refers to a material that can absorb moisture, can expand as it takes up water, and is composed of more than one component. In some embodiments, the material comprises a hygroscopic component. One of skill will appreciate that a composite material can take several forms. In some embodiments, for example, the terms "composite material" and "composite structure" can be used interchangeably. Wood is a natural material comprised of cellulose, hemicelluloses, and lignin components, making the wood structure a composite material or a composite structure. Wood is also a composite in that it not only has a number of components having different compositions but also a morphology that includes a composite of structural components such as pores, void spaces, vessels, and the like. Synthetic materials fabricated from multiple components, each having the same or different compositions, are another example. Such materials can include woven and non-woven materials having a composite of numerous fibrous elements that each have the same or different individual compositions. Composite materials can also include a combination of natural and synthetic materials as components. Plywood, particle board, and wafer board are some examples of composite materials that can include both synthetic and natural components, as well as have composite materials arranged as a composite structure. In some embodiments, a composite material can have a uniform structure in that it comprises a blend of components such as, for example, a blend of polymers that produce a desired chemical and/or physical characteristic when blended.

The hygroexpansive, composite material can experience a change in volume as moisture enters and leaves the material. In some embodiments, the change in volume can be a shrinkage in the volume of the material that occurs when the material has a reduction in moisture content. In materials comprising wood, for example, shrinkage normally begins at about the fiber saturation point, where the fiber saturation point can sometimes be reached at around 30% by weight moisture content. In some embodiments, the relationship between the shrinkage and reduction in moisture content can be a continuous and fairly linear relationship when moisture content reductions occur at or below about 35% by weight, at or below about 30% by weight, at or below about 25% by weight, at or below about 20% by weight, at or below about 15% by weight, at or below about 7% by weight, or any range therein.

The radiation generally refers to any radiation known to one of skill that can penetrate materials tested using the methods taught herein. One of skill can readily select an appropriate source of radiation and will appreciate that the radiation should have an intensity that is sufficient to penetrate through a depth of the composite material. The radiation selected will depend on the material test and can be any of a variety of wavelengths of radiation in the electromagnetic spectrum. In some embodiments, the radiation can be x-radiation or gamma radiation. In the methods taught herein, a portion of the radiation is absorbed by the composite material, and a remaining portion of the radiation is transmitted from an exit surface of the composite material. The distance between the entry surface and the exit surface can be considered as the depth of the composite material that was penetrated by the electromagnetic radiation. In some embodiments, the radiation is selected to match the mass attenuation coefficient of the composite material with the mass attenuation coefficient of water.

In some embodiments, the radiation is x-radiation produced using an x-ray tube that can operate under a range of kilovoltage (kV) selections, milliamperage (mA) selections, and exposure time selections. The kilovoltage selection provides the wavelength of the radiation and helps to control the ability of the radiation to penetrate the composite material, where a higher kilovoltage produces a shorter wavelength and a lower kilovoltage produces a longer wavelength. One of skill can appreciate that a shorter wavelength can generally provide better penetration and, potentially, shorter exposure times. Given the nature and density of the material, one of skill can readily select a desired kilovoltage for a particular application. In some embodiments, the kilovoltage selection ranges from about 30 kV to about 350 kV, from about 35 kV to about 300 kV, from about 40 kV to about 250 kV, from about 35 kV to about 200 kV, from about 35 kV to about 150 kV, from about 35 kV to about 120 kV, from about 40 kV to about 120 kV, from about 45 kV to about 120 kV, from about 55 kV to about 100 kV, from about 35 kV to about 80 kV, from about 60 kV to about 85 kV, or any range therein.

One of skill will also appreciate that the selection of kV affects the type of scatter radiation that is produced during the collision of the photons with the composite material. In some embodiments, a higher kV can produce a Compton radiation, a lower kV can produce photoelectric radiation, and a range of kV in-between likewise provided a range of mixtures of the types of scatter radiation produced. One of skill can take these factors into account when selecting a kV range for use with a particular composite material, as well as a means of collimating and/or filtering the radiation transmitted by a radiation source and/or received by a radiation detector.

One of skill will also appreciate that the mA and exposure time are selected such that the combination to provides the amount of radiation needed to penetrate the depth of the composite material. The selection of mA and time will vary according to the composite material being tested and taking into consideration the source of radiation used. For example, less x-ray will typically be necessary when the source of radiation uses a triple-phase power source as opposed to a single-phase power source. Use of a filter at the source of the radiation can also improve the quality of the radiation transmitted by removing soft rays from the hard rays during an exposure period. Such an exposure may not reduce the exposure time necessary, but it may increase the accuracy of measurements, for example, by reducing the amount of unnecessary scatter radiation produced and collected by the radiation detector. Such implements can also be used to enhance the safety to operators during operation of the system.

The density of the composite material can then be measured in the hygroexpansive state by (i) passing the radiation through the composite material and (ii) measuring the amount of absorbed radiation. Using this technique, the amount of absorbed radiation provides a measure of the density of the composite material in the hygroexpansive state.

The "density" of the composite material can refer to the weight per unit volume of the material, where the volume of the material includes the cumulative volume of all components of the composite material. The "hygroexpansive state" is the volumetric state of the material at a particular moisture content and includes the density and volume of the material at the particular moisture content. The "amount of absorbed radiation" can generally be determined using the difference between the amount of radiation emitted into the entry surface of the composite material less the amount of radiation transmitted from the exit surface of the composite material. The teachings set-forth herein refer to the amount of absorbed radiation providing the density of a hygroexpansive, composite material; however, it should be appreciated by one of skill that the teachings may interchangeably refer the amount of absorbed radiation providing the information used to calculate a corresponding density of a hygroexpansive, composite material.

One of skill will appreciate that wood, for example, swells or shrinks with absorption or loss of water, respectively, and that the density of wood should be expressed, in some embodiments, at a specified moisture content and corresponding volume. As such, the conditions can include the minimum (oven-dry or moisture-free) weight and the maximum (green) or the minimum (oven-dry or moisture-free) volume. In some embodiments, the maximum volume basis is the hygroexpansive state. In some embodiments, the specimen is considered to have swollen to its maximum volume when its moisture content exceeds the "fiber-saturation point," which lies between 18 and 26% by weight (wet basis) for some species of wood. Procedures for obtaining the volume, moisture content, and density, in both green and oven-dry samples of a hygroscopic, composite material, can be determined, for example, using TAPPI TEST METHOD T 258 om-06.

One of skill will appreciate that wood, for example, has an equilibrium moisture content that depends on the temperature and relative humidity of its environment. The equilibrium moisture content (EMC) occurs when the wood has reached a water content equilibrium with its environment and is no longer gaining or losing moisture. The following formula can provide an expected moisture content of a wood material knowing the temperature and relative humidity of the environment surrounding the wood:

$$M=1800/W\ [KH/(1-KH)+(K_1KH+2K_1K_2K^2H^2)/(1+K_1KH+K_1K_2K^2H^2)]$$

where:
M=moisture content (weight %);
T=temperature (° F.);
H relative humidity (%) $W=330+0.452T+0.00415T^2$;
$K=0.791+0.000463T-0.000000844T^2$;
$K_1=6.34+0.000775T-0.0000935T^2$; and,
$K_2=1.09+0.0284T-0.0000904T^2$ Table 1 provides example EMC values for a representative range of atmospheric conditions, and the values are considered to be applicable to a variety of wood species for most practical purposes.

TABLE 1

| Relative Humidity (%) | Ambient Air Temperature (° F.) | | | | | | | | | | |
|---|---|---|---|---|---|---|---|---|---|---|---|
|  | 30 | 40 | 50 | 60 | 70 | 80 | 90 | 100 | 110 | 120 | 130 |
| 5 | 1.4 | 1.4 | 1.4 | 1.3 | 1.3 | 1.3 | 1.2 | 1.2 | 1.1 | 1.1 | 1.0 |
| 10 | 2.6 | 2.6 | 2.6 | 2.5 | 2.5 | 2.4 | 2.3 | 2.3 | 2.2 | 2.1 | 2.0 |
| 15 | 3.7 | 3.7 | 3.6 | 3.6 | 3.5 | 3.5 | 3.4 | 3.3 | 3.2 | 3.0 | 2.9 |
| 20 | 4.6 | 4.6 | 4.6 | 4.6 | 4.5 | 4.4 | 4.3 | 4.2 | 3.0 | 3.9 | 3.7 |
| 25 | 5.5 | 5.5 | 5.5 | 5.4 | 5.4 | 5.3 | 5.1 | 5.0 | 4.9 | 4.7 | 4.5 |
| 30 | 6.3 | 6.3 | 6.3 | 6.2 | 6.2 | 6.1 | 5.9 | 5.8 | 5.6 | 5.4 | 5.2 |
| 35 | 7.1 | 7.1 | 7.1 | 7.0 | 6.9 | 6.8 | 6.7 | 6.5 | 6.3 | 6.1 | 5.9 |
| 40 | 7.9 | 7.9 | 7.9 | 7.8 | 7.7 | 7.6 | 7.4 | 7.2 | 7.0 | 6.8 | 6.6 |
| 45 | 8.7 | 8.7 | 8.7 | 8.6 | 8.5 | 8.3 | 8.1 | 7.9 | 7.7 | 7.5 | 7.2 |
| 50 | 9.5 | 9.5 | 9.5 | 9.4 | 9.2 | 9.1 | 8.9 | 8.7 | 8.4 | 8.2 | 7.9 |

TABLE 1-continued

| Relative Humidity (%) | Ambient Air Temperature (° F.) | | | | | | | | | |
|---|---|---|---|---|---|---|---|---|---|---|
| 55 | 10.4 | 10.4 | 10.3 | 10.2 | 10.1 | 9.9 | 9.7 | 9.5 | 9.2 | 8.9 | 8.7 |
| 60 | 11.3 | 11.3 | 11.2 | 11.1 | 11.0 | 10.8 | 10.5 | 10.3 | 10.0 | 9.7 | 9.4 |
| 65 | 12.4 | 12.3 | 12.3 | 12.1 | 12.0 | 11.7 | 11.5 | 11.2 | 11.0 | 10.6 | 10.3 |
| 70 | 13.5 | 13.5 | 13.4 | 13.3 | 13.1 | 12.9 | 12.6 | 12.3 | 12.0 | 11.7 | 11.3 |
| 75 | 14.9 | 14.9 | 14.8 | 14.6 | 14.4 | 14.2 | 13.9 | 13.6 | 13.2 | 12.9 | 12.5 |
| 80 | 16.5 | 16.5 | 16.4 | 16.2 | 16.0 | 15.7 | 15.4 | 15.1 | 14.7 | 14.4 | 14.0 |
| 85 | 18.5 | 18.5 | 18.4 | 18.2 | 17.9 | 17.7 | 17.3 | 17.0 | 16.6 | 16.2 | 15.8 |
| 90 | 21.0 | 21.0 | 20.9 | 20.7 | 20.5 | 20.2 | 19.8 | 19.5 | 19.1 | 18.6 | 18.2 |
| 95 | 24.3 | 24.3 | 24.3 | 24.1 | 23.9 | 23.6 | 23.3 | 22.9 | 22.4 | 22.0 | 21.5 |
| 98 | 26.9 | 26.9 | 26.9 | 26.8 | 26.6 | 26.3 | 26.0 | 25.6 | 25.2 | 24.7 | 24.2 |

A baseline density of a representative sample of the composite material is then measured in a water-free state, and the density is obtained by passing the radiation through the representative sample and measuring the amount of absorbed radiation. The amount of absorbed radiation, again, provides the information to calculate the density of the composite material, but this time it represents the density of the material in the water-free state.

The "baseline density" of the material in the water-free state represents the composite material in the water-free state. A material can be considered to be in "a water-free state" when the water component of the material has been substantially removed using any water removal process known to one of skill in the art, as long as the process provides a water-free density measurement that is a statistically acceptable fit to the moisture content/density relationship for the hygroexpansive, composite material. One of skill can determine whether the water-free density measurement is an outlier, whether the measurement is a statistically acceptable fit, with respect to the moisture content/density relationship knowing the accuracy and precision desired for a given use of the measurement design.

One of skill will appreciate that water can be retained in a composite structure for a variety of physical reasons that include, for example, the hygroscopicity of the material, capillary pressures resulting from the physical morphology of the composite structure, and entrapment of the water within the structure. In some embodiments, removal of all of the water could only occur by applying conditions that may adversely affect the structure of the composite material, such that it is no longer representative of the material as it was selected for a particular end use. A partially combusted wood sample, for example, would not be representative of a wood structure as it was intended for most end uses, such as a structural component of a piece of furniture. Likewise, a "green" piece of wood that was freshly cut from a live tree would contain too much water and would not be representative of a wood structure as it was intended for most end uses. In some embodiments, a "substantial amount" of water has been removed to produce a water-free state of a composite material when the water has been removed to an extent necessary for one of skill to consider the composite material to be representative of the material in a water-free state, while maintaining the structure of the material as it was selected for a particular end use.

In some embodiments, a process that is used to produce the representative sample in the water-free state is oven drying, solvent exchange, vacuum drying, critical point drying, or a combination thereof. In some embodiments, the process is oven drying at about 100° C., about 101° C., about 102° C., about 103° C., about 104° C., about 105° C., about 106° C., about 107° C., about 108° C., about 109° C., any sequential combination of these temperatures, or any cyclical or graduated range of these temperatures, wherein the temperatures can be applied at any of a variety of predetermined time increments. The predetermined time increments can be selected, for example, to simulate an industrial scale water removal process, and the time increments can vary with moisture content changes during drying. The drying process can be dynamic, in that the location and size of the area on the composite material that is heated can also vary as the moisture moves throughout the composite material during a drying process, as determined using the methods and/or apparatus taught herein.

In order to translate the density accurately into a moisture content, a volumetric shrinkage of the representative sample that occurs during the removal of the amount of water from the representative material can be measured and factored in the calculation as a dimensional compensation. Use of the volumetric shrinkage provides a novel way of calculating an accurate representative moisture content of the composite material in the hygroexpansive state. As such, the calculating can include using (1) the density of the composite material in the hygroexpansive state, (2) the density of the representative sample in the water-free state, and (3) the volumetric shrinkage of the representative sample in the water-free state.

One of skill will appreciate that removal of water can change the volume of a hygroexpansive material, and the change in volume will affect the density calculations, as well as the ultimate moisture content and profile calculations. In some embodiments, the volumetric shrinkage ranges from about 0.1% to about 80%, from about 0.2% to about 75% from about 0.2% to about 50%, from about 5% to about 45%, from about 2% to about 25%, from about 2% to about 15%, from about 2% to about 10%, from about 2% to about 5%, or any range therein. In some embodiments, between the fiber saturation point and the ovendry state, wood will only change by about 0.1% to about 0.3% of its dimension along the grain, by about 2% to about 8% across the grain and across the annular rings, and about 5% to about 15% across the grain and parallel to the annular rings.

In some embodiments, the teachings are directed to a nondestructive method of measuring a moisture content profile across a dimension of a hygroexpansive, composite material. The method comprises selecting a hygroexpansive, composite material having an amount of water that needs to be removed prior to a predetermined end-use of the composite material and selecting a radiation source for emitting a thin collimated beam of an electromagnetic radiation into an entry surface of the composite material.

Figure 2:
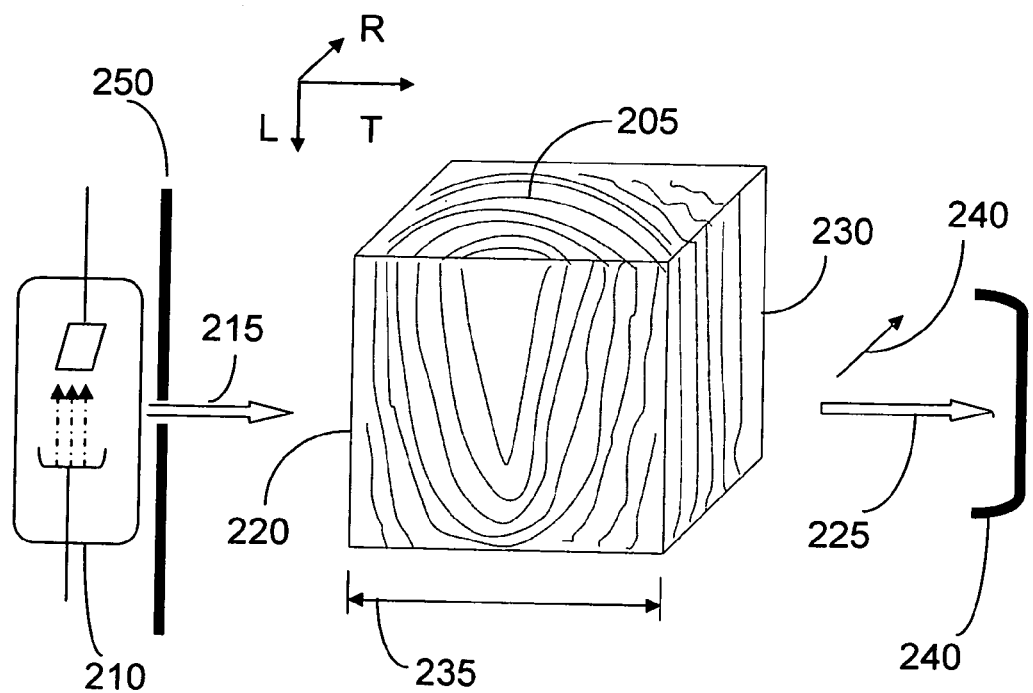
FIG. 2 illustrates the use of the method to measure a moisture content profile across a dimension of a wood material according to some embodiments.

FIG. 2 illustrates the use of the method to measure a moisture content profile across a dimension of a wood material according to some embodiments. The wood material 205 is selected, and a radiation source 210 is selected for emitting electromagnetic radiation 215 into an entry surface 220 of the wood material 205 in a hygroexpansive state. Collimator 250 is provided to emit a thin beam of radiation. A portion of the radiation 215 is absorbed by the wood material 205, and a remainder 225 of the radiation 215 is transmitted from an exit surface 230 of the wood material 205. The distance 235 is the depth of the wood material 205 that was penetrated by the radiation 215. A representative sample of the wood material 205 is used to again measure the amount of radiation 215 that is transmitted from the representative sample in a water-free state and collected by a radiation detector 240. The amount of radiation 215 that is transmitted from the wood material 205 in the hygroexpansive state represents the density of the wood material 205 in the hygroexpansive state, and the amount of radiation 215 that is transmitted from the wood material 205 in the water-free state represents the density of the wood material 205 in the water-free state. As above, the volumetric shrinkage is used as a dimensional compensation to correlate the density with a moisture content value. In this embodiment, the density of the wood and the representative sample is taken across scanning direction 245 at a plurality of locations in the scanning direction 245, wherein a profile of the amount of absorbed radiation at each location across the scanning direction 245 provides the information to calculate the density profile of the hygroexpansive state, as well as the density profile of the water-free state. In some embodiments, the density at each location across the scanning direction 245 of the representative sample in the water-free state is substantially the same, and a single point can be used in the moisture calculations to produce a moisture profile of the wood material. Note that in FIG. 2, the designators "R", "L", and "T" represent the radial, longitudinal, and tangential directions across the wood material as would be commonly understood by those of skill in the art, and this directionality is provided for purposes of example only without intending to limit the teachings provided herein in any way.

The "thin collimated beam" provides a resolution control for the moisture content profiles obtained using the methods taught herein and is measured where the emitted radiation enters the entry surface of the composite material. In some embodiments, the width of the beam can range from about 0.001 inches to about 0.20 inches, from about 0.002 inches to about 0.020 inches, from about 0.002 inches to about 0.01 inches, from about 0.002 inches to about 0.008 inches, from about 0.003 inches to about 0.005 inches, or any range therein. In some embodiments, the beam can have a length that ranges from about 0.05 inches to about 5.0 inches, from about 0.5 inches to about 4.0 inches, from about 1.0 inches to about 3.0 inches, from about 1.5 inches to about 2.5 inches, or any range therein. In some embodiments, the beam can be square, rectangular, circular, elliptical, triangular, or any dimensions desired or practical for a particular material being tested. In some embodiments, the collimator for the beam can be located directly at the source of the radiation, at the exit location of the radiation from the housing of the source, at the entry surface of the composite material, or anywhere between the composite material and the radiation source. In some embodiments, the thin collimated beam has a width ranging from about 0.001 inches to about 0.020 inches and a length ranging from about 0.25 inches to about 4.0 inches at the entry surface of a hygroexpansive, composite material.

These embodiments further include measuring a density profile of the composite material in a hygroexpansive state, wherein the density profile is obtained by (i) passing the radiation through the composite material and across a scanning direction of the composite material and (ii) measuring the amount of absorbed radiation at a plurality of locations across the scanning direction. In these embodiments, a profile of the amount of absorbed radiation at each location across the scanning direction provides the information to calculate the density profile of the composite material in the hygroexpansive state.

These embodiments further include measuring a baseline density profile of a representative sample of the composite material in a water-free state, wherein the density profile is obtained by (i) passing the radiation through the representative sample and across a scanning direction of the representative sample and (ii) measuring the amount of absorbed radiation at a plurality of locations across the scanning direction. A profile of the amount of absorbed radiation at each location can be used to simulate the baseline density profile of the composite material in the water-free state. As described above, these embodiments further include determining a volumetric shrinkage of the representative sample that occurs during the removal of the amount of water from the representative material to simulate a volumetric shrinkage of the composite material that occurs during removal of the amount of water. A moisture content profile of the composite material in the hygroexpansive state is then developed. Developing the moisture content profile includes calculating the moisture content at each of a plurality of points across the scanning direction of the composite material using (1) the density at each point across the scanning direction of the composite material in the hygroexpansive state, (2) the density at each point across the scanning direction of the representative sample in the water-free state, and (3) the volumetric shrinkage of the representative sample that occurs during the removal of the amount of water.

In some embodiments, the teachings are directed to a method of measuring moisture movement in a hygroexpansive, composite material during a water removal, process. In these embodiments, the method comprises using the method of measuring a moisture content profile, as described above, to develop a first moisture content profile across the scanning direction at a first time, $t_1$; and repeating the method of measuring a moisture content profile at subsequent times $t_2$ through $t_n$, in a water removal process, wherein n is an integer greater than 2, times $t_2$ to $t_n$ each represent a period of time at which to measure subsequent moisture content profiles of each of a series of hygroexpansive states of the composite material that occur during the course of the water removal process, and $t_n$ represents the time at which the amount of water has been removed from the composite material. In these embodiments, the repeating provides a series of moisture content profiles that, when visualized together, provides a measure of the moisture movement in the hygroexpansive, composite material.

In some embodiments, the teachings are directed to a method of improving a process of removing water from a hygroexpansive, composite material. In these embodiments, the method comprises using the method of measuring moisture movement, as described above, and altering process variables in the water removal process to obtain desired moisture content profiles at times $t_1$ through $t_n$, wherein the variables are selected from a group consisting of variables in the design of a water removal apparatus such as, for example, the location of heating elements, temperature control devices, processing speed control devices, and airflow control devices; variables in the operation of the water removal apparatus such as, for example, time to temperature, time at temperature, cool down time, temperature ramping, temperature cycling, etc; and variables in the design of the composite material such as, for example, selection of the components in the material, relative quantities of the components selected, positioning of the components with respect to dimensional stability, and the like.

In some embodiments, the hygroexpansive, composite material comprises a wood component. In some embodiments, the process of removing water from a composite material is in the form of a kiln and the composite material is a product comprising a wood component. In some embodiments, the hygroexpansive, composite material is a particleboard or a waferboard. In some embodiments, the hygroexpansive, composite material is plywood.

In some embodiments, the measuring of the density profile of the composite material in the hygroexpansive state is continuous, in that the density profile is obtained by continuously (i) passing the radiation through the composite material and across the scanning direction of the composite material and continuously (ii) measuring the amount of absorbed radiation continuously across the scanning direction. In these embodiments, the profile of the amount of absorbed radiation across the scanning direction provides a continuous density profile of the composite material in the hygroexpansive state; and wherein, the repeating is done as described above and provides a series of continuous moisture content profiles that, when visualized together, provides a measure of the moisture movement in the hygroexpansive, composite material. In some embodiments, the baseline density across the scanning direction is substantially the same at each location, and the density at a single location is used as a constant baseline density in the calculation of moisture content.

In some embodiments, the teaching is directed to an apparatus for detecting moisture content profiles of a hygroexpansive composite material. In these embodiments, the apparatus comprises a radiation source that is positioned for emitting an electromagnetic radiation in a first direction into an entry surface of a composite material in a hygroexpansive state. The radiation source can be any source considered useful by one of skill in the art for a particular composite material, as described above, where the radiation has an intensity that is sufficient to penetrate through a depth of the composite material and transmit a remainder of the radiation from an exit surface of the composite material. And, the distance between the entry surface and the exit surface is the depth of the composite material that was penetrated by the radiation.

In these embodiments, the apparatus also comprises a radiation detector that is positioned for processing the transmitted radiation from the first direction, wherein the processing includes (1) detecting the amount of electromagnetic radiation that penetrated the depth of the composite material and transmitted to the detector, and (2) converting the amount of radiation that transmitted to the detector into a digital signal corresponding to a density at a location in the composite material. As described above, the density is used in computing the moisture content at the location in the composite material.

In these embodiments, the apparatus also comprises a mechanism for moving the radiation source and the radiation detector in a scanning direction across a dimension of the composite material to acquire a series of the digital signals across the scanning direction. One of skill will appreciate that there are numerous configurations possible, as long as the radiation detector is positioned to collect the radiation transmitted from the exit surface of the hygroexpansive material. In some embodiments, the radiation source and radiation detector can both be on a single unit platform, for example, in which both move on the same plane and in the same direction as a result of being part of single unit platform. In some embodiments, the radiation source and the radiation detector can be independent units, and each can move independently to allow additional equipment design freedom, such that the equipment is limited by the need for a single unit platform. In such embodiments, each independent unit needs to be synchronized to move in a complementary fashion to the other unit, and the focal distance between the two units, or the distance between the source of radiation and the detector, would remain the same. If the focal distance varies, then the intensity of the radiation must be compensated to reflect this change in focal distance. One of skill can readily utilize the inverse square law to accommodate for such variations, within reason.

In some embodiments, a computation system is included for translating each digital signal produced by the radiation detector in the scanning direction into the moisture content profile using (1) a density profile taken across the scanning direction of the composite material in the hygroexpansive state, (2) a density profile taken across the scanning direction of a representative sample of the composite material in a water-free state, and (3) a measure of volumetric shrinkage of the representative sample that occurs during the removal of the amount of water from the representative material.

Figure 3:
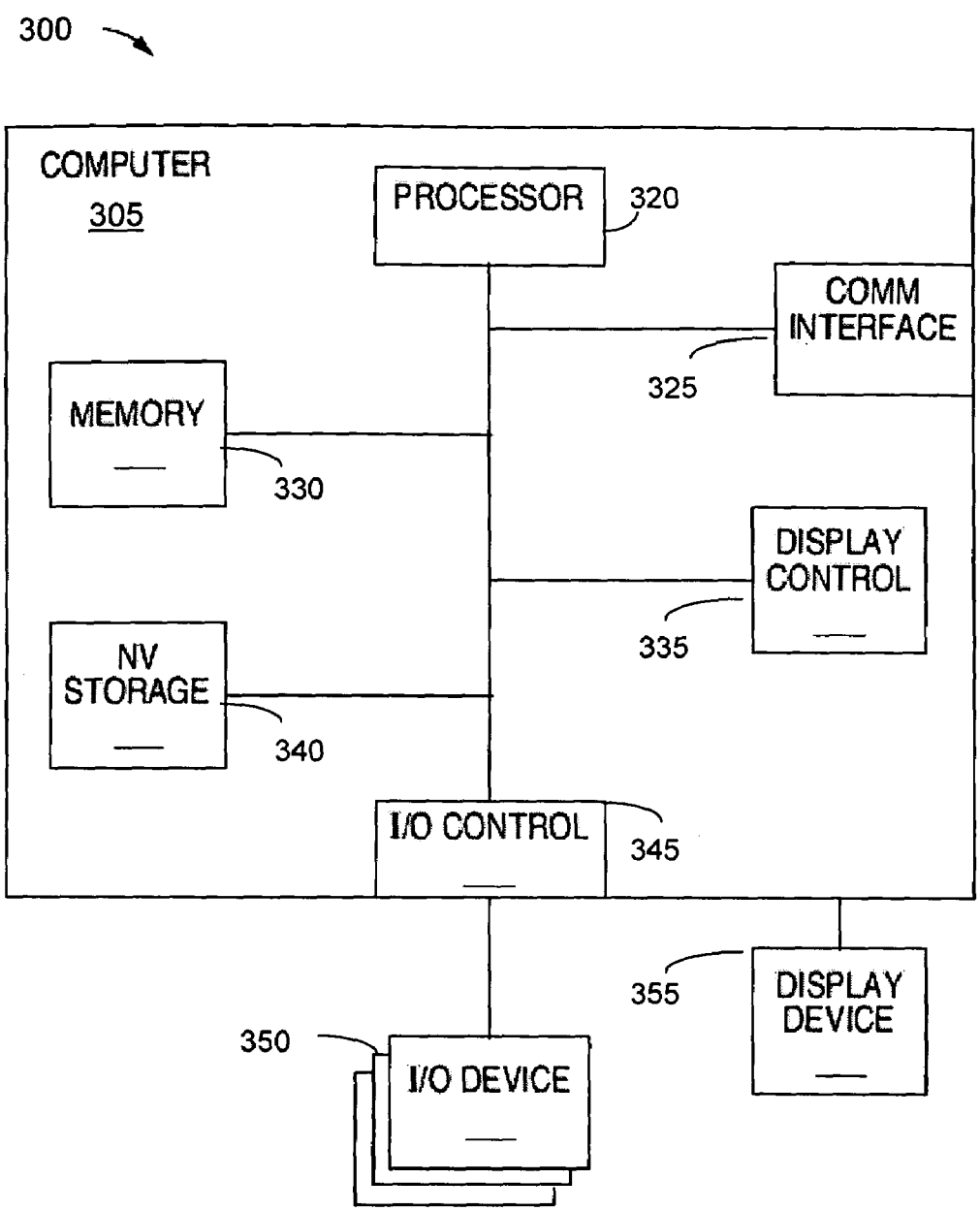
FIG. 3 depicts the general technology platform of a device containing the computer system for a multilingual teaching of numeric or language skills according to some embodiments.

FIG. 3 depicts the general technology platform of a device containing the computer system for a multilingual teaching of numeric or language skills according to some embodiments. The computer system 300 may be a conventional computer system and includes a computer 305, I/O devices 350, and a display device 355. The computer 305 can include a processor 320, a communications interface 325, memory 330, display control 335, non-volatile storage 340, and I/O control 345. The computer system 300 may be coupled to or include the I/O devices 350 and display device 355.

The computer 305 interfaces to external systems through the communications interface 325, which may include a modem or network interface. It will be appreciated that the communications interface 325 can be considered to be part of the computer system 300 or a part of the computer 305. The communications interface 325 can be an analog modem, integrated services digital network (ISDN) modem, cable modem, token ring interface, satellite transmission interface (e.g. "direct PC"), or other interfaces for coupling the computer system 300 to other computer systems.

The processor 320 may be, for example, a conventional microprocessor such as an Intel Pentium microprocessor or Motorola power PC microprocessor. The memory 330 is coupled to the processor 320 by a bus. The memory 330 can be dynamic random access memory (DRAM) and can also include static ram (SRAM). The bus couples the processor 320 to the memory 330, also to the non-volatile storage 340, to the display control 335, and to the I/O control 345.

The I/O devices 350 can include a keyboard, disk drives, printers, a scanner, and other input and output devices, including a mouse or other pointing device. The display control 335 may control in the conventional manner a display on the display device 355, which can be, for example, a cathode ray tube (CRT) or liquid crystal display (LCD). The display control 335 and the I/O control 345 can be implemented with conventional well known technology.

The non-volatile storage 340 is often a magnetic hard disk, an optical disk, or another form of storage for large amounts of data. Some of this data is often written by a direct memory access process into memory 330 during execution of software in the computer 305. One of skill in the art will immediately recognize that the terms "machine-readable medium" or "computer-readable medium" includes any type of storage device that is accessible by the processor 320 and also encompasses a carrier wave that encodes a data signal.

Objects, methods, inline caches, cache states and other object-oriented components may be stored in the non-volatile storage 340, or written into memory 330 during execution of, for example, an object-oriented software program.

The computer system 300 is one example of many possible computer systems which have different architectures. For example, personal computers based on an Intel microprocessor often have multiple buses, one of which can be an I/O bus for the peripherals and one that directly connects the processor 320 and the memory 330 (often referred to as a memory bus). The buses are connected together through bridge components that perform any necessary translation due to differing bus protocols.

Network computers are another type of computer system that can be used. Network computers do not usually include a hard disk or other mass storage, and the executable programs are loaded from a network connection into the memory 330 for execution by the processor 320. A typical computer system will usually include at least a processor, memory, and a bus coupling the memory to the processor.

In addition, the computer system 300 is controlled by operating system software which includes a file management system, such as a disk operating system, which is part of the operating system software. One example of an operating system software with its associated file management system software is the family of operating systems known as Windows® from Microsoft Corporation of Redmond, Wash., and their associated file management systems. Another example of operating system software with its associated file management system software is the Linux operating system and its associated file management system. The file management system is typically stored in the non-volatile storage 340 and causes the processor 320 to execute the various acts required by the operating system to input and output data and to store data in memory, including storing files on the non-volatile storage 340.

In some embodiments, the teachings are directed to an apparatus for detecting moisture movement in a hygroexpansive composite material, wherein the apparatus comprises the apparatus for detecting moisture content profiles. In these embodiments, the computation system further comprises a translation engine embodied in a computer readable medium that calculates moisture movement by calculating moisture content profiles at each of times $t_1$ through $t_n$; wherein, n is an integer, $t_1$ through $t_n$ each represent a period of time at which to moisture content profiles of each of a series of hygroexpansive states of the composite material that occur at times $t_1$ through $t_n$ during the water removal process, and $t_n$ represents the time at which the amount of water has been removed from the composite material. In these embodiments, the computer system further comprises an automation module embodied in a computer readable medium for converting input parameters into an automated motion of the radiation source and the radiation detector, wherein the input parameters include scanning time, scanning speed, and scanning position. And, in some embodiments, the computer system further comprises a display.

Figure 4:
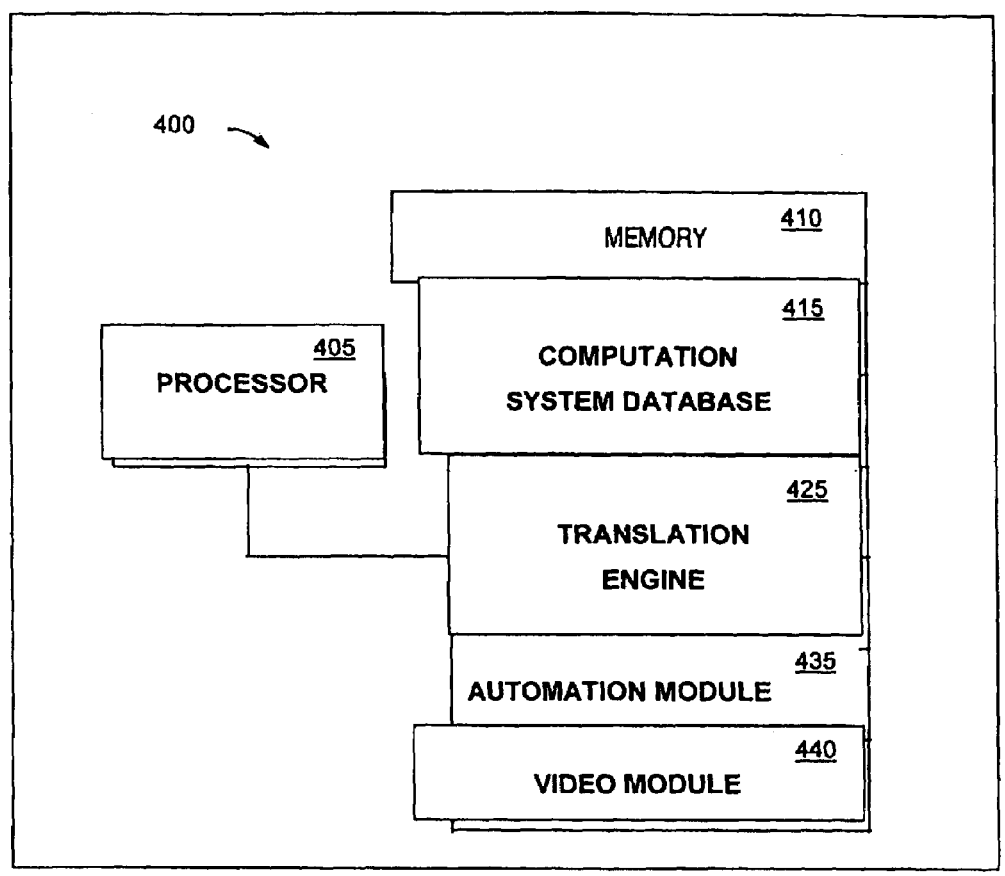
FIG. 4 illustrates a processor-memory diagram to describe the major memory modules processed according to some embodiments.

FIG. 4 illustrates a processor-memory diagram to describe the major memory modules processed according to some embodiments. The system 400 shown in FIG. 4 contains a processor 405 and a memory 410 (that can include non-volatile memory). The memory 410 includes a computation system database 415 embodied in a computer readable medium. In some embodiments, the memory 410 also contains a translation engine 425 embodied in a computer readable medium that calculates moisture movement by calculating moisture content profiles at each of times $t_1$ through $t_n$; wherein, n is an integer, $t_1$ through $t_n$ each represent a period of time at which to moisture content profiles of each of a series of hygroexpansive states of the composite material that occur at times $t_1$ through $t_n$ during the water removal process, and $t_n$ represents the time at which the amount of water has been removed from the composite material. In some embodiments, the memory also contains an automation module 435 embodied in a computer readable medium for converting input parameters into an automated motion of the radiation source and the radiation detector, wherein the input parameters include, but are not limited to, scanning time, scanning speed, and scanning position. And, in some embodiments, the computer system further comprises a display, wherein the system can include a video display module 440 to show an operator system data, such as, for example, input operating parameters and output measurements and profiles.

Accordingly, in some embodiments, the teachings are directed to an apparatus for detecting moisture movement in a hygroexpansive composite material, wherein the apparatus comprises the apparatus for detecting moisture content profiles. In these embodiments, the computation system described above further comprises a translation engine embodied in a computer readable medium that calculates moisture movement by calculating moisture content profiles at each of times $t_1$ through $t_n$; wherein, n is an integer, $t_1$ through $t_n$ each represent a period of time at which to moisture content profiles of each of a series of hygroexpansive states of the composite material that occur at times $t_1$ through $t_n$ during the water removal process, and $t_n$ represents the time at which the amount of water has been removed from the composite material. In these embodiments, the computer system further comprises an automation module embodied in a computer readable medium for converting input parameters into an automated motion of the radiation source and the radiation detector, wherein the input parameters include scanning time, scanning speed, and scanning position. And, in some embodiments, the computer system further comprises a display.

The following examples are merely illustrative and in are not intended to be limiting in any way.

EXAMPLE 1

As described herein, calculations have been derived for correlating wood density to moisture content using dimensional compensation. A typical source detector configuration for measuring density profile across a thickness of a wood material has been shown in FIGS. 1 and 2. As shown in FIG. 2, the radiation beam is passed through a slit to provide a collimated beam which penetrates the wood and a representative sample of the wood. The method can be used to incrementally scan the wood and the representative sample of the wood at multiple sites across a scanning direction. Using this data, a density profile can be obtained.

Figure 5:
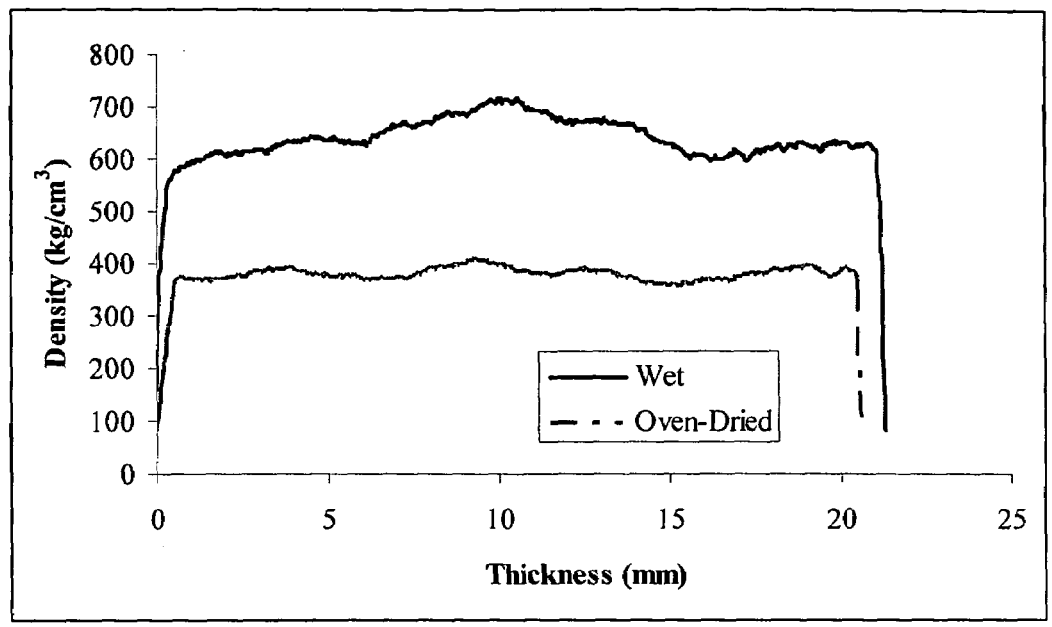
FIG. 5 shows typical density profiles for an oven-dried sample and the same sample profiled wet, at moisture content m according to some embodiments.
Figure 5:
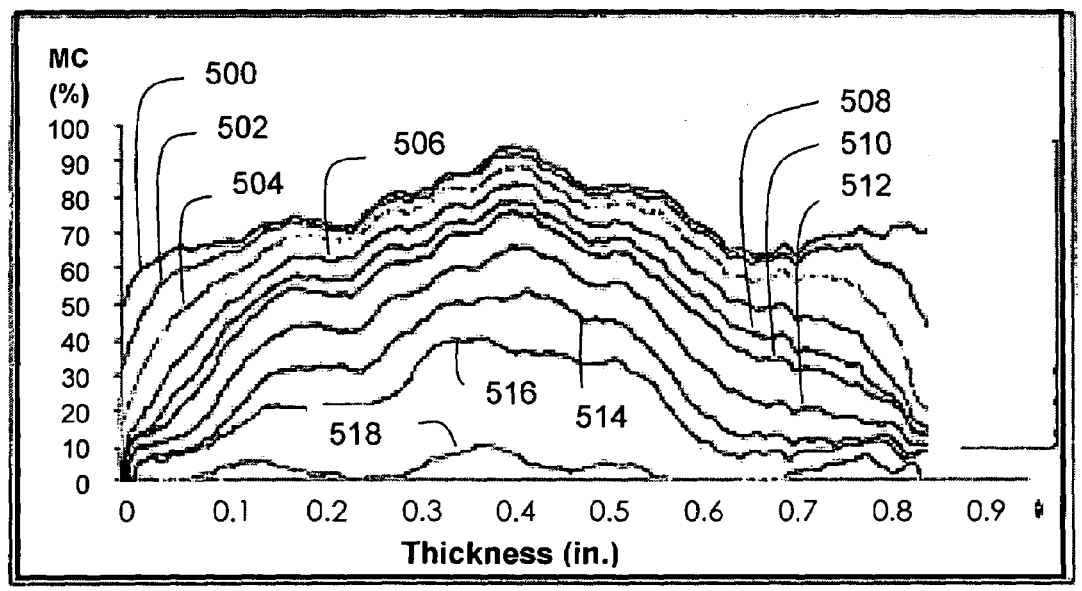

FIGS. 5a and 5b show a typical drying behavior according to some embodiments. In FIG. 5a, density profiles for an oven-dried sample and the same sample profiled in a wet state at moisture content m are illustrated. Comparing the two profiles, the following equations can be used to determine the moisture gradient across the scanning direction.

$$\text{when } m \geq 30\%: \quad m = \frac{\rho_m - \rho_0}{\rho_0} \times 100$$

-continued $$\text{when } m < 30\%: \; m = \frac{\rho_m - \rho_0}{\rho_0} \times 100 \times \frac{1}{\left(1 - \frac{10\rho_m S_0}{3\rho_0(1 - S_0)}\right)}$$

where, m is the moisture content in weight percent, $\rho_0$ is the density of the water-free sample, $\rho_m$ is the density of the wood at moisture content m, $S_0$ is the total volumetric shrinkage in the wood that occurs when removing the water from the wood using oven drying at 105° C.

Since there are dimensional changes with changes in moisture content in the wood, the two profiles are matched to ensure $\rho_0$ and $\rho_m$ provide a dimensional compensation based on a volumetric shrinkage. The following equation represents the volumetric shrinkage relationship between the shrinkage of the wood from a green state to a moisture content of less than about 30%, and the total shrinkage from the green state to an oven-dried state using a temperature of 105° C.:

$$S_m = S_0 \left(\frac{30 - m}{30}\right),$$

where, $S_0$ is the total volumetric shrinkage in the wood that occurs when removing the water from the wood using oven drying at 105° C., and $S_m$ is the volumetric shrinkage of the wood from a green state to a moisture content of less than about 30%.

FIG. 5b illustrates moisture gradients in a wood sample at different points of time during a drying process. Curve 500 represents the wood sample at 0 minutes, curve 502 represents the wood sample at 5 minutes, curve 504 represents the wood sample at 15 minutes, curve 506 represents the wood sample at 30 minutes, curve 508 represents the wood sample at 45 minutes, curve 510 represents the wood sample at 60 minutes, curve 512 represents the wood sample at 90 minutes, curve 514 represents the wood sample at 120 minutes, and curve 516 represents the wood sample at 150 minutes, curve 518 represents the wood sample at 200 minutes.

EXAMPLE 2

Eight solid wood samples (four oak samples, two pine samples, and two spruce samples) with nominal dimension of 50.8×50.8×20.3 mm (longitudinal×tangential×radial, or L×T×R) were equilibrated at 22° C. and 65% relative humidity and tested to verify the techniques taught herein. The equilibrated samples were then edge-sealed with a sealer and oven-dried for 24 hours under temperature of 105° C. Their oven-dried density profiles were measured using QMS X-RAY DENSITY PROFILER (Knoxville, Tenn.).

The samples were placed in water with one L×T face submerged, and about half of each sample immersed in the water to purposely induce moisture gradients in the radial direction of the samples. The samples were taken out of the water at different time intervals for density profile measurements as shown in FIG. 1.

Figure 6:
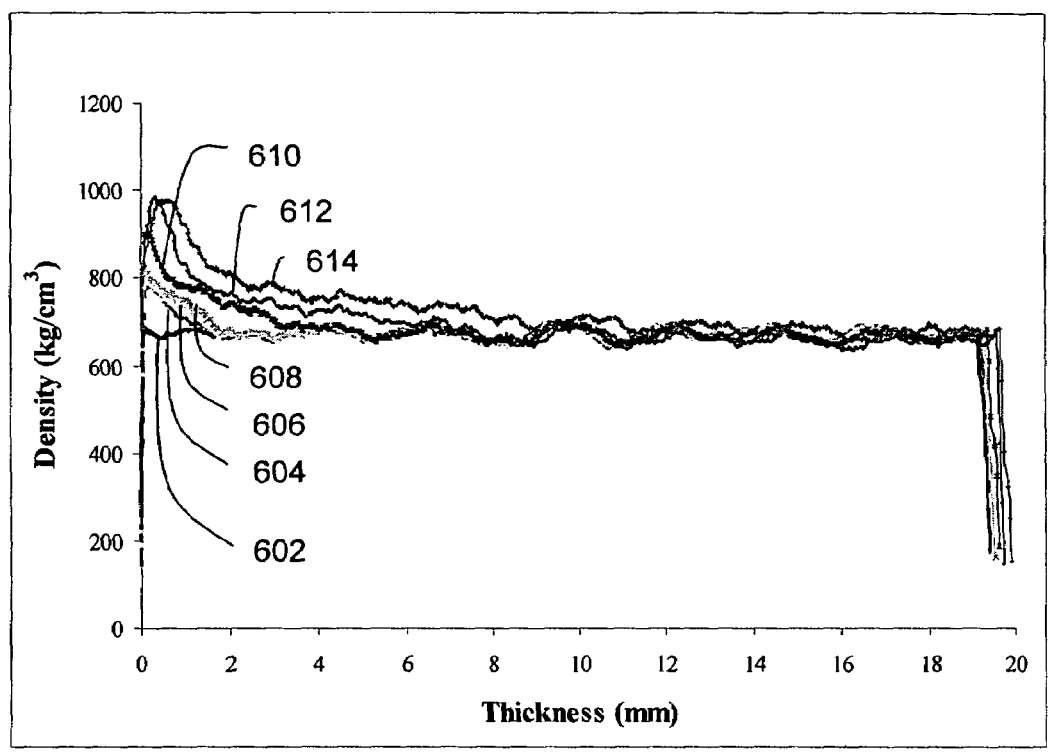
FIG. 6 shows density profiles at different intervals for a typical oak sample having an induced moisture penetration from one side of the sample according to some embodiments.

FIG. 6 shows density profiles at different intervals for a typical oak sample having an induced moisture penetration from one side of the sample according to some embodiments. After obtaining samples having from 1 hr to 7 days immersion, all samples were sliced in its radial direction with a microtome knife. Each sliced layer (about 1 mm thick) was carefully marked and oven-dried to provide simulated moisture content profiles by measuring the moisture content of each microtomed lamina gravimetrically. The data was obtained and plotted against a radial direction to provide a measure of the actual incremental moisture gradient in that direction. There were about twelve to fourteen layers sliced from the surface that was immersed in the water. Curve 602 represents an oven-dried sample, curve 604 represents 1 hour immersion, curve 606 represents 3 hours immersion, curve 608 represents 5 hours immersion, curve 610 represents 1 day immersion, and curve 610 represents 4 days immersion, curve 612 represents 7 days immersion.

EXAMPLE 3

Figure 7:
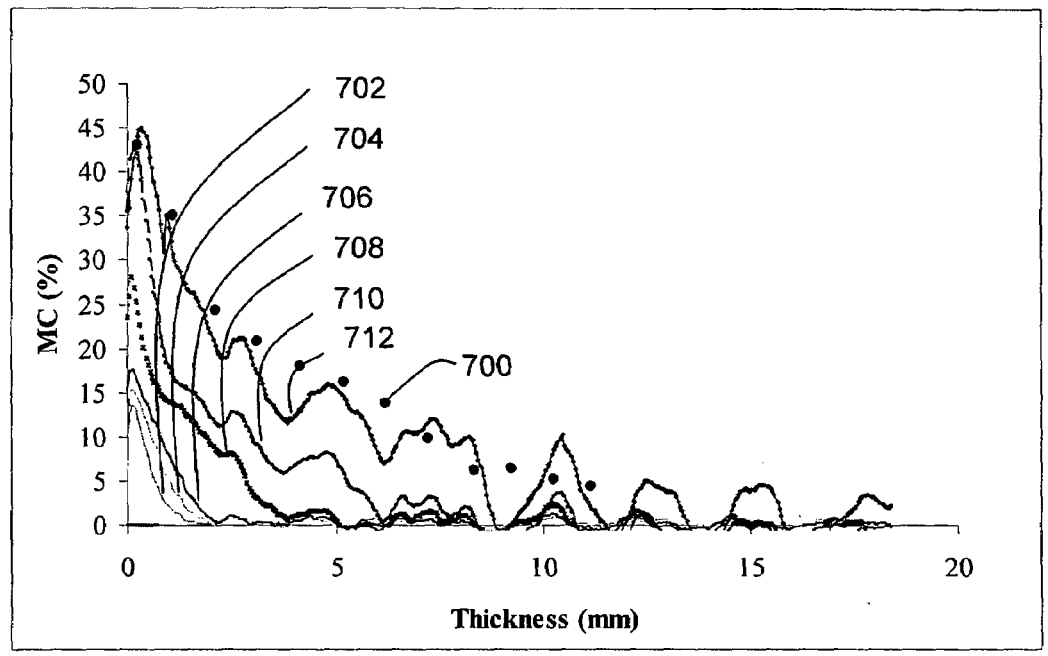
FIG. 7 shows the simulated and measured moisture gradients for the same specimen of Oak 1 according to some embodiments.

FIG. 7 shows the simulated and measured moisture gradients for the same specimen of Oak 1 according to some embodiments. The simulated moisture gradient was determined using the microtome oven-dry method described above in Example 2 after 7-days of immersing the sample in water. The measured moisture gradients were determined using the x-ray profile measurement techniques taught herein. Curve 700 represents the simulated, microtomed sample that was immersed 7 days. Curve 702 represents 1 hour immersion, curve 704 represents 3 hours immersion, curve 706 represents 5 hours immersion, curve 708 represents 1 day immersion, curve 710 represents 4 days immersion, and curve 712 represents 7 days immersion, each of which was profiled using the radiation method taught herein.

The measured gradients in FIG. 7 contain "noise" due to the difficulty in matching $\rho_0$ and $\rho_m$ as the wood volume changes. Without intending to be bound by any theory or mechanism of action, it is contemplated that the mismatch results in a slight offset between the $\rho_m$ profile and the $\rho_0$ profile. In addition, dimensional changes, such as warp, twist, and cup during moisture absorption, along with density differences between latewood and earlywood may also contribute to the mismatches between the $\rho_m$ profile and the $\rho_0$ profile.

Figure 8:
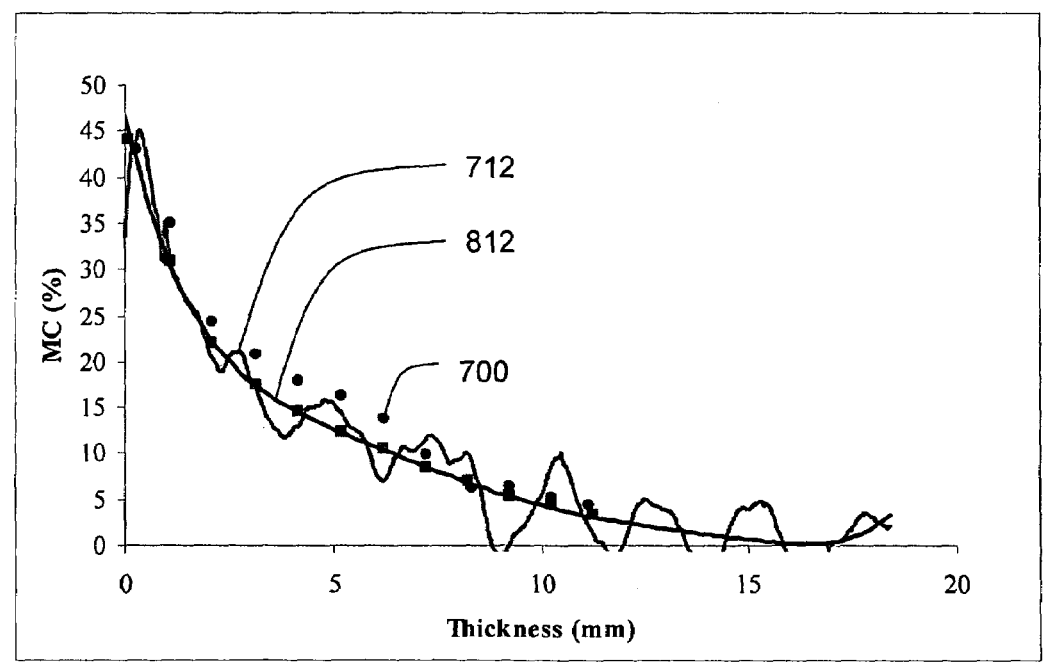
FIG. 8 illustrates how smoothing through a polynomial regression provides excellent results according to some embodiments.

The gradient measured using the methods taught herein correlated well with the simulated gradient. FIG. 8 illustrates how smoothing through a polynomial regression provides excellent results according to some embodiments. The gradient that was measured using the methods taught herein was smoothed using a polynomial regression method as shown in FIG. 8, where curves 700 and 712 are the same curves as shown in FIG. 7. Table 2 shows correlation coefficients between gradients measured using the methods taught herein and the simulated gradients. The high correlation (average R-square after smoothing is 0.97) indicates that the radiation method taught herein provides an accurate and rapid estimation of moisture content across a scanning direction of a sample.

TABLE 2

| Wood ID | Linear Regression | | | Linear Regression after Smoothing | | |
|---|---|---|---|---|---|---|
| | Slopes | Intercepts | R-square | Slopes | Intercepts | R-square |
| Oak1 | 0.94 | 3.20 | 0.93 | 1.01 | 1.85 | 0.98 |
| Oak2 | 0.94 | 5.81 | 0.81 | 1.11 | 2.55 | 0.97 |
| Oak3 | 0.78 | 12.58 | 0.32 | 1.16 | 1.72 | 0.95 |
| Oak4 | 1.11 | 3.34 | 0.79 | 1.12 | −0.16 | 0.96 |
| Pine1 | 1.07 | 13.79 | 0.70 | 1.11 | −0.46 | 0.98 |
| Pine2 | 0.80 | 13.96 | 0.98 | 1.01 | 4.68 | 0.99 |
| Spruce1 | 0.77 | 4.50 | 0.97 | 0.80 | 3.57 | 0.98 |
| Spruce2 | 1.19 | 0.25 | 0.98 | 1.10 | 0.95 | 0.98 |

EXAMPLE 4

The examples provide above illustrate the manner in which the methods taught herein can provide a very powerful and useful tool for understanding internal moisture movement and moisture-related stress development in hygroexpansive, composite materials.

Figure 9:
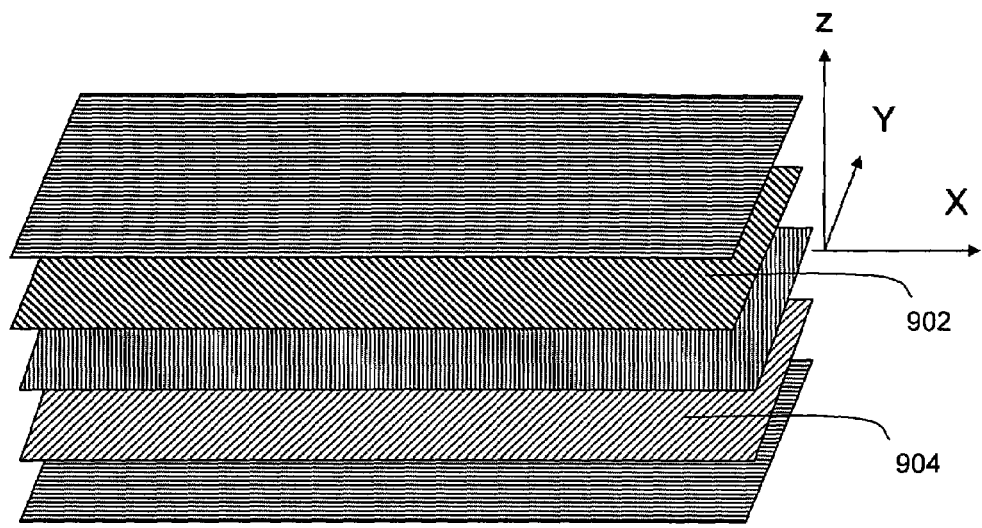
FIG. 9 illustrates a 5-layer hygroexpansive, composite wood material having different grain directions according to some embodiments.

FIG. 9 illustrates a 5-layer hygroexpansive, composite wood material having different grain directions according to some embodiments. The grain directions of the second layer 902 and fourth layer 904 are +/−45° from the x-y coordinates, such that this product as a whole is called a 0/45/90/−45/0 balanced construction. In some embodiments, as described above, between the fiber saturation point and the ovendry state, wood will only change by about 0.1% to about 0.3% of its dimension along the grain, by about 2% to about 8% across the grain and across the annular rings, and about 5% to about 15% across the grain and parallel to the annular rings. As such, the balanced construction is necessary to balance the stresses associated with volumetric changes in the composite wood structure.

Figure 10:
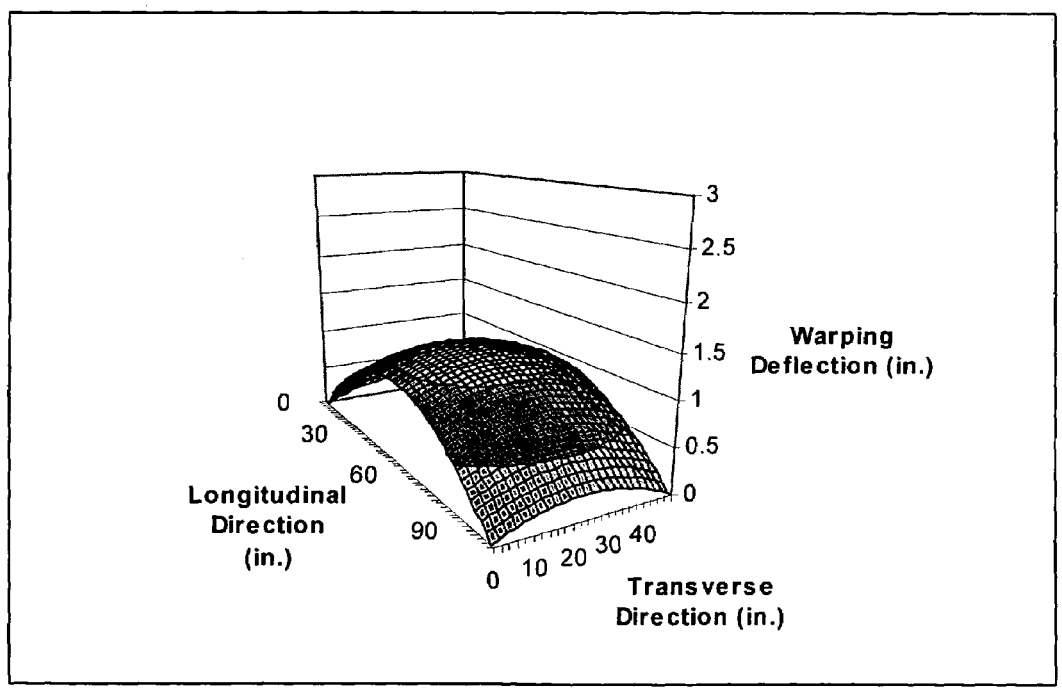
FIG. 10 illustrates a typical plate warping of a 4'×8' unbalanced panel as simulated using a computer program.

FIG. 10 illustrates a typical plate warping of a 4'×8' unbalanced panel as simulated using a computer program. As can be seen, from this example, the 0/45/90/−45/0 balanced construction is designed to balance the stresses involved with the hygroexpansive behavior that results in unacceptable warping, sometimes referred to as center deflection, of the product.

One of skill will appreciate that having prompt information available about internal moisture content gradients could help to dynamically control and design wood drying processes. The information of the moisture distribution inside a wood product could also assist in the understanding of the warping behavior of wood composite structures and provide engineers with a tool to help diagnose and find solutions that inhibit or prevent dimensional instability in wood products.

I claim:

1. A non-destructive method of measuring a moisture content in a hygroexpansive material, the method comprising:
    selecting a hygroexpansive, composite material having an amount of water that results in a hygroexpansive state of the material;
    selecting a radiation source for emitting electromagnetic radiation into an entry surface of the composite material; wherein the radiation has an intensity that is sufficient to penetrate through a depth of the composite material, a portion of the radiation is absorbed by the composite material, and a remainder of the radiation is transmitted from an exit surface of the composite material; wherein the distance between the entry surface and the exit surface is the depth of the composite material that was penetrated by the electromagnetic radiation;
    measuring a density of the composite material in the hygroexpansive state, wherein the density is obtained by (i) passing the radiation through the composite material and (ii) measuring the amount of absorbed radiation, wherein the amount of absorbed radiation provides the density of the composite material in the hygroexpansive state;
    measuring a baseline density of a representative sample of the composite material in a water-free state, wherein the density is obtained by passing the radiation through the representative sample and measuring the amount of absorbed radiation, wherein the amount of absorbed radiation provides the density of the composite material in the water-free state;
    determining a volumetric shrinkage of the representative sample that occurs during the removal of the amount of water from the representative material; and,
    calculating a moisture content of the composite material in the hygroexpansive state, wherein the calculating includes using (1) the density of the composite material in the hygroexpansive state, (2) the density of the representative sample in the water-free state, and (3) the volumetric shrinkage of the representative sample in the water-free state.

2. A non-destructive method of measuring a moisture content profile across a dimension of a hygroexpansive, composite material, wherein the method comprises:
    selecting a hygroexpansive, composite material having an amount of water that needs to be removed prior to a predetermined end-use of the composite material;
    selecting a radiation source for emitting a thin collimated beam of an electromagnetic radiation into an entry surface of the composite material;
        wherein the radiation has an intensity that is sufficient to penetrate through a depth of the composite material, a portion of the radiation is absorbed by the composite material, and a remainder of the radiation is transmitted from an exit surface of the composite material; wherein the distance between the entry surface and the exit surface is the depth of the composite material that was penetrated by the radiation;
    measuring a density profile of the composite material in a hygroexpansive state, wherein the density profile is obtained by (i) passing the radiation through the composite material and across a scanning direction of the composite material and (ii) measuring the amount of absorbed radiation at a plurality of locations across the scanning direction, wherein a profile of the amount of absorbed radiation at each location across the scanning direction provides the density profile of the composite material in the hygroexpansive state;
    measuring a baseline density profile of a representative sample of the composite material in a water-free state, wherein the density profile is obtained by (i) passing the radiation through the representative sample and across a scanning direction of the representative sample and (ii) measuring the amount of absorbed radiation at a plurality of locations across the scanning direction, wherein a profile of the amount of absorbed radiation at each location simulates the baseline density profile of the composite material in the water-free state;
    determining a volumetric shrinkage of the representative sample that occurs during the removal of the amount of water from the representative material to simulate a volumetric shrinkage of the composite material that occurs during removal of the amount of water; and,
    developing a moisture content profile of the composite material in the hygroexpansive state, wherein the developing includes calculating the moisture content at each point across the scanning direction of the composite material using (1) the density at each point across the scanning direction of the composite material in the hygroexpansive state, (2) the density at each point across the scanning direction of the representative sample in the water-free state, and (3) the volumetric shrinkage of the representative sample that occurs during the removal of the amount of water.

3. A method of measuring moisture movement in a hygroexpansive, composite material during a water removal process, wherein the method comprises:

using the method of claim 2 to develop a first moisture content profile across the scanning direction at a first time, $t_1$; and repeating the method of claim 2 at subsequent times $t_2$ through $t_n$ in a water removal process, wherein n is an integer greater than 2, times $t_2$ to $t_n$ each represent a period of time at which to measure subsequent moisture content profiles of each of a series of hygroexpansive states of the composite material that occur during the course of the water removal process, and $t_n$ represents the time at which the amount of water has been removed from the composite material; wherein the repeating provides a series of moisture content profiles that, when visualized together, provides a measure of the moisture movement in the hygroexpansive, composite material.

4. A method of improving a process of removing water from a hygroexpansive, composite material, wherein the method comprises:

using the method of claim 3, and altering process variables in the water removal process to obtain desired moisture content profiles at times $t_1$ through $t_n$, wherein the variables are selected from a group consisting of variables in the design of a water removal apparatus, variables in the operation of the water removal apparatus, variables in the design of the composite material.

5. The method of claim 3, wherein the hygroexpansive, composite material comprises a wood component.

6. The method of claim 3, wherein the hygroexpansive, composite material is a particleboard or a waferboard.

7. The method of claim 3, wherein the hygroexpansive, composite material is plywood.

8. The method of claim 3, wherein the electromagnetic radiation is x-radiation.

9. The method of claim 3, wherein the electromagnetic radiation is gamma radiation.

10. The method of claim 3, wherein the thin collimated beam has a width ranging from about 0.001 inches to about 0.020 inches and a length ranging from about 0.25 inches to about 4.0 inches at the entry surface of the hygroexpansive, composite material.

11. The method of claim 3, wherein the radiation is x-radiation produced using a kilovoltage ranging from about 35 kV to about 300 kV.

12. The method of claim 3, wherein the volumetric shrinkage ranges from about 2% to about 5%.

13. The method of claim 3, wherein the baseline density across the scanning direction is substantially the same at each location, and the density at a single location is used as a constant baseline density in the calculation of moisture content.

14. The method of claim 3, wherein the measuring of the density profile of the composite material in the hygroexpansive state is continuous, in that the density profile is obtained by continuously (i) passing the radiation through the composite material and across the scanning direction of the composite material and (ii) continuously measuring the amount of absorbed radiation across the scanning direction, wherein the profile of the amount of absorbed radiation across the scanning direction provides a continuous density profile of the composite material in the hygroexpansive state; and wherein, the repeating provides a series of continuous moisture content profiles that, when visualized together, provides a measure of the moisture movement in the hygroexpansive, composite material.

15. An apparatus for detecting moisture content profiles of a hygroexpansive composite material, wherein the apparatus comprises:

a radiation source that is positioned for emitting an electromagnetic radiation in a first direction into an entry surface of a composite material in a hygroexpansive state, wherein the radiation has an intensity that is sufficient to penetrate through a depth of the composite material and transmit a remainder of the radiation from an exit surface of the composite material, wherein the distance between the entry surface and the exit surface is the depth of the composite material that was penetrated by the radiation;

a radiation detector that is positioned for processing the transmitted radiation from the first direction, wherein the processing includes (1) detecting the amount of electromagnetic radiation that penetrated the depth of the composite material and transmitted to the detector, and (2) converting the amount of radiation that transmitted to the detector into a digital signal corresponding to a density at a location in the composite material, and the density is used in computing the moisture content at the location in the composite material;

a mechanism for moving the radiation source and the radiation detector in a scanning direction across a dimension of the composite material to acquire a series of the digital signals across the scanning direction; and a computation system for translating each digital signal produced by the radiation detector in the scanning direction into the moisture content profile using (1) a density profile taken across the scanning direction of the composite material in the hygroexpansive state, (2) a density profile taken across the scanning direction of a representative sample of the composite material in a water-free state, and (3) a measure of volumetric shrinkage of the representative sample that occurs during the removal of the amount of water from the representative material.

16. An apparatus for detecting moisture movement in a hygroexpansive composite material, wherein the apparatus comprises the apparatus of claim 15; wherein the computation system further comprises a translation engine embodied in a computer readable medium that calculates moisture movement by calculating moisture content profiles at each of times $t_1$ through $t_n$; wherein, n is an integer, $t_1$ through $t_n$ each represent a period of time at which to moisture content profiles of each of a series of hygroexpansive states of the composite material that occur at times $t_1$ through $t_n$ during the water removal process, and $t_n$ represents the time at which the amount of water has been removed from the composite material;

an automation module embodied in a computer readable medium for converting input parameters into an automated motion of the radiation source and the radiation detector, wherein the input parameters include scanning time, scanning speed, and scanning position; and, a display.

17. A non-destructive method of measuring a moisture content profile across a dimension of a material comprising wood, wherein the method comprises:

selecting a material comprising wood, wherein the material has an amount of water that needs to be removed prior to a predetermined end-use of the composite material;

selecting a radiation source for emitting a thin collimated beam of an electromagnetic radiation into an entry surface of the material; wherein the radiation has an intensity that is sufficient to penetrate through a depth of the material, a portion of the radiation is absorbed by the material, and a remainder of the radiation is transmitted from an exit surface of the material; wherein the distance between the entry surface and the exit surface is the depth of the material that was penetrated by the radiation;

measuring a density profile of the material in a hygroexpansive state, wherein the density profile is obtained by (i) passing the radiation through the material and across a scanning direction of the material and (ii) measuring the amount of absorbed radiation at a plurality of locations across the scanning direction, wherein a profile of the amount of absorbed radiation at each location across the scanning direction provides the density profile of the material in the hygroexpansive state;

measuring a baseline density profile of a representative sample of the material in a water-free state, wherein the density profile is obtained by (i) passing the radiation through the representative sample and across a scanning direction of the representative sample and (ii) measuring the amount of absorbed radiation at a plurality of locations across the scanning direction, wherein a profile of the amount of absorbed radiation at each location simulates the baseline density profile of the material in the water-free state;

determining a volumetric shrinkage of the representative sample that occurs during the removal of the amount of water from the representative sample to simulate a volumetric shrinkage of the material that occurs during removal of the amount of water; and, developing a moisture content profile of the material in the hygroexpansive state, wherein the developing includes calculating the moisture content at each point across the scanning direction of the material using (1) the density at each point across the scanning direction of the material in the hygroexpansive state, (2) the density at each point across the scanning direction of the representative sample in the water-free state, and (3) the volumetric shrinkage of the representative sample that occurs during the removal of the amount of water.

18. A method of measuring moisture movement in a material comprising wood during a water removal process, wherein the method comprises:

using the method of claim 17 to develop a first moisture content profile across the scanning direction at a first time, $t_1$; and repeating the method of claim 17 at subsequent times $t_2$ through $t_n$, in a water removal process, wherein n is an integer greater than 2, times $t_2$ to $t_n$ each represent a period of time at which to measure subsequent moisture content profiles of each of a series of hygroexpansive states of the material that occur during the course of the water removal process, and $t_n$ represents the time at which the amount of water has been removed from the material; wherein the repeating provides a series of moisture content profiles that, when visualized together, provides a measure of the moisture movement in the material.

19. The method of claim 17, wherein the material is a particleboard or a waferboard.

20. The method of claim 17, wherein the material is plywood.

21. The method of claim 17, wherein the electromagnetic radiation is x-radiation.

22. The method of claim 17, wherein the electromagnetic radiation is gamma radiation.

23. The method of claim 17, wherein the thin collimated beam has a width ranging from about 0.001 inches to about 0.020 inches and a length ranging from about 0.25 inches to about 4.0 inches at the entry surface of the material.

24. The method of claim 17, wherein the radiation is x-radiation produced using a kilovoltage ranging from about 35 kV to about 300 kV.

25. The method of claim 17, wherein the baseline density across the scanning direction is substantially the same at each location, and the density at a single location is used as a constant baseline density in the calculation of moisture content.

26. The method of claim 17, wherein the measuring of the density profile of the composite material in the hygroexpansive state is continuous, in that the density profile is obtained by continuously (i) passing the radiation through the composite material and across the scanning direction of the composite material and (ii) continuously measuring the amount of absorbed radiation across the scanning direction, wherein the profile of the amount of absorbed radiation across the scanning direction provides a continuous density profile of the composite material in the hygroexpansive state; and wherein, the repeating provides a series of continuous moisture content profiles that, when visualized together, provides a measure of the moisture movement in the hygroexpansive, composite material.

27. The method of claim 17, wherein the calculating includes use of the equation $$m = \frac{\rho_m - \rho_0}{\rho_0} \times 100,$$

when $m \geq 30\%$, and
use of the equation $$m = \frac{\rho_m - \rho_0}{\rho_0} \times 100 \times \frac{1}{\left(1 - \frac{10\rho_m S_0}{3\rho_0(1-S_0)}\right)},$$

when $m < 30\%$.

28. The method of claim 18, wherein the calculating includes use of the equation $$m = \frac{\rho_m - \rho_0}{\rho_0} \times 100,$$

when $m \geq 30\%$, and
use of the equation $$m = \frac{\rho_m - \rho_0}{\rho_0} \times 100 \times \frac{1}{\left(1 - \frac{10\rho_m S_0}{3\rho_0(1-S_0)}\right)},$$

when $m < 30\%$.

29. A method of improving a process of removing water from a material comprising wood, wherein the method comprises:

using the method of claim 17, and altering process variables in the water removal process to obtain desired moisture content profiles at times $t_1$ through $t_n$, wherein the variables are selected from a group consisting of variables in the design of a water removal apparatus, variables in the operation of the water removal apparatus, variables in the design of the material.

30. An apparatus for detecting moisture content profiles of a material comprising wood, wherein the apparatus comprises:

a radiation source that is positioned for emitting an electromagnetic radiation in a first direction into an entry surface of a material comprising wood in a hygroexpansive state, wherein the radiation has an intensity that is sufficient to penetrate through a depth of the material and transmit a remainder of the radiation from an exit surface of the material, wherein the distance between the entry surface and the exit surface is the depth of the material that was penetrated by the radiation;

a radiation detector that is positioned for processing the transmitted radiation from the first direction, wherein the processing includes (1) detecting the amount of electromagnetic radiation that penetrated the depth of the material and transmitted to the detector, and (2) converting the amount of radiation that transmitted to the detector into a digital signal corresponding to a density at a location in the material, and the density is used in computing the moisture content at the location in the material;

a mechanism for moving the radiation source and the radiation detector in a scanning direction across a dimension of the material to acquire a series of the digital signals across the scanning direction; and a computation system for translating each digital signal produced by the radiation detector in the scanning direction into the moisture content profile using (1) a density profile taken across the scanning direction of the material in the hygroexpansive state, (2) a density profile taken across the scanning direction of a representative sample of the material in a water-free state, and (3) a measure of volumetric shrinkage of the representative sample that occurs during the removal of the amount of water from the representative sample.

31. An apparatus for detecting moisture movement in a material comprising wood, wherein the apparatus comprises the apparatus of claim 30, wherein the computation system further comprises a translation engine embodied in a computer readable medium that calculates moisture movement by calculating moisture content profiles at each of times $t_1$ through $t_n$; wherein, n is an integer, $t_1$ through $t_n$ each represent a period of time at which to moisture content profiles of each of a series of hygroexpansive states of the material that occur at times $t_1$ through $t_n$ during the water removal process, and $t_n$ represents the time at which the amount of water has been removed from the material;

an automation module embodied in a computer readable medium for converting input parameters into an automated motion of the radiation source and the radiation detector, wherein the input parameters include scanning time, scanning speed, and scanning position; and, a display.

* * * * *